(12) United States Patent
Sakairi

(10) Patent No.: US 8,921,776 B2
(45) Date of Patent: Dec. 30, 2014

(54) ION DETECTING DEVICE

(75) Inventor: Minoru Sakairi, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/429,910

(22) Filed: Mar. 26, 2012

(65) Prior Publication Data

US 2012/0248306 A1    Oct. 4, 2012

(30) Foreign Application Priority Data

Apr. 1, 2011    (JP) .................. 2011-081384

(51) Int. Cl.
*H01J 49/00*    (2006.01)
*G01N 33/497*    (2006.01)
*G01N 15/06*    (2006.01)

(52) U.S. Cl.
CPC ........ *G01N 33/4972* (2013.01); *B60W 2540/24* (2013.01); *G01N 15/0656* (2013.01)
USPC ............................ 250/288; 250/281; 250/282

(58) Field of Classification Search
None
See application file for complete search history.

(56) References Cited

U.S. PATENT DOCUMENTS

| | | | |
|---|---|---|---|
| 6,124,592 A * | 9/2000 | Spangler | 250/287 |
| 6,177,668 B1 * | 1/2001 | Hager | 250/282 |
| 6,278,111 B1 * | 8/2001 | Sheehan et al. | 250/288 |
| 7,619,214 B2 * | 11/2009 | Miller et al. | 250/288 |
| 8,056,395 B2 * | 11/2011 | Oki | 73/31.07 |
| 2003/0216660 A1 * | 11/2003 | Ben-Oren et al. | 600/532 |
| 2004/0031917 A1 * | 2/2004 | Hager | 250/282 |
| 2004/0206910 A1 * | 10/2004 | Lee et al. | 250/397 |
| 2005/0085740 A1 * | 4/2005 | Davis et al. | 600/532 |

FOREIGN PATENT DOCUMENTS

| | | | | |
|---|---|---|---|---|
| JP | 7-325020 A | 12/1995 | | |
| JP | 2000-510638 A | 8/2000 | | |
| JP | 2003-257328 A | 9/2003 | | |
| JP | 2003257328 A * | 9/2003 | | H01J 27/02 |
| JP | 2006-510905 A | 3/2006 | | |

* cited by examiner

*Primary Examiner* — Andrew Smyth
(74) *Attorney, Agent, or Firm* — Crowell & Moring LLP

(57) ABSTRACT

The present invention provides a small-sized ion detecting device that quickly and simply performs mass analysis under atmospheric pressure. Accordingly, electrodes are arranged and held in the ion detecting device so as to be able to detect water clusters in ambient air with a high sensitivity. Thereby, ions can be detected even in a spatially-restricted place.

10 Claims, 20 Drawing Sheets

ABSOLUTE VALUE OF PEAK INTENSITY
(RELATIVE VALUE OF PEAK INTENSITY)

ION DETECTING DEVICE

CLAIM OF PRIORITY

The present application claims priority from Japanese patent application JP2011-081384 filed on Apr. 1, 2011, the content of which is hereby incorporated by reference into this application.

BACKGROUND OF THE INVENTION

1. Field of the Invention

The present invention relates to a detecting device based on ion detection under atmospheric pressure. For example, the present invention relates to a device for anti-drunk-driving in a mobile object such as an automobile based on the detecting technique. Further, the present invention relates to measurement of a person and ambient air.

2. Description of the Related Art

In the conventional technical field of breath detection and breath alcohol detection, there is a method in which target substances are ionized to be detected by a mass analyzing unit existing in vacuum.

U.S. Pat. No. 6,278,111 discloses a method in which minute droplets generated by an ionization method called an electrospray method are introduced into a second chamber in vacuum, the droplets are allowed to hit gas introduced from an upper part in the chamber to prompt desolvation, and mass analysis is performed for the desolvation ions.

Japanese Patent Application Laid-Open Publication No. H07-325020 discloses a method in which the current of ions that flow into a skimmer cone under vacuum and/or a lens electrode of a following ion focusing lens and that are generated under atmospheric pressure is detected, and voltage applied to the electrode is controlled so as to keep the current of ions constant.

Japanese Patent Application Laid-Open Publication No. 2003-257328 describes a method in which ions generated in vacuum are allowed to be largely deflected to hit an electrode, so that an optical system can be cleaned.

Japanese Patent Application Laid-Open Publication No. 2006-510905 describes a method in which ions introduced in vacuum are aerodynamically converged.

Japanese Patent Application Laid-Open Publication No. 2000-510638 describes an ion trap mass spectrometer for efficiently trapping ions in vacuum US Patent Application Publication No. 2004031917 describes a method in which the S/N ratio of a detection signal is improved in a tandem mass spectrometer using an atmospheric pressure ionization method.

In any of the above cases, it is assumed that ions are introduced in vacuum for detection.

SUMMARY OF THE INVENTION

In any of the above methods, a mass spectrometer that is operated under high vacuum is used to analyze generated ions. Use of the mass spectrometer enables measurement of the mass number of ions and enables analysis with a high degree of accuracy. However, in order to precisely separate ions according to the ion number in a magnetic or electric field as the mass spectrometer does, it is necessary to avoid the following as much as possible: changing of ion trajectories caused by target ions hitting neutral molecules; or dissolving of target ions by hitting. In addition, it is necessary to considerably reduce the number of existing neutral molecules while setting the inside of the mass spectrometer at a high vacuum of $10^{-2}$ Pa or smaller. Further, in order to detect target ions with a high sensitivity, the amplifying effect of electrons is used by applying high voltage as in a secondary electron multiplier. Thus, if the mass spectrometer is not set in a high vacuum state, electric discharge occurs at the detector portion and ions cannot be detected, which is one of the reasons that the mass spectrometer is set in a high vacuum state. Therefore, a vacuum discharging system such as a turbo-molecular pump or a rotary pump needs to be provided, leading to a problem of an increase in the size of the device.

As described above, it has been necessary to provide a vacuum discharging system such as a turbo-molecular pump in order to separate ions according to the mass number in a magnetic or electric field in the conventional technique, and thus the device has been increased in size. At this time, the force acting on ions is the force by a magnetic or electric field, and has no relation to the force of gravitation.

In order to address the above-described problems, the following configuration is exemplified as an example of the present invention.

The present invention provides an ion detecting device including: an inlet through which ambient air is introduced into a casing that is placed under atmospheric pressure; a detection electrode that detects part of deflected charged-particles contained in the ambient air introduced into the casing through the inlet; and a voltage applying electrode, wherein the detection electrode and the voltage applying electrode are arranged in parallel in the direction of the force of gravitation, an electrode holding unit holding the detection electrode and the voltage applying electrode is provided, and the electrode holding unit is made of material with a water absorption rate of 0.4 or smaller.

Further, as another example, the present invention provides an ion detecting device including: an inlet through which gas is introduced into a casing that is placed under atmospheric pressure; a first electrode that traps ions and a second electrode that can apply voltage, the first electrode and the second electrode forming an inflow channel for the introduced gas in the direction of the force of gravitation in the casing; a current measurement device that is connected to the first electrode; and a data analyzing device that analyzes components contained in the gas on the basis of a measurement result by the current measurement device, wherein an electrode holding unit holding the first electrode and the second electrode is provided, and the electrode holding unit is made of material with a water absorption rate of 0.4 or smaller.

The analyzing method allows the device to operate under atmospheric pressure. Thus, it is not necessary to provide a large-sized vacuum discharging system such as a turbo-molecular pump and the device can be considerably downsized. Accordingly, the problems can be addressed.

DETAILED DESCRIPTION OF THE INVENTION

First Embodiment

Figure 1:
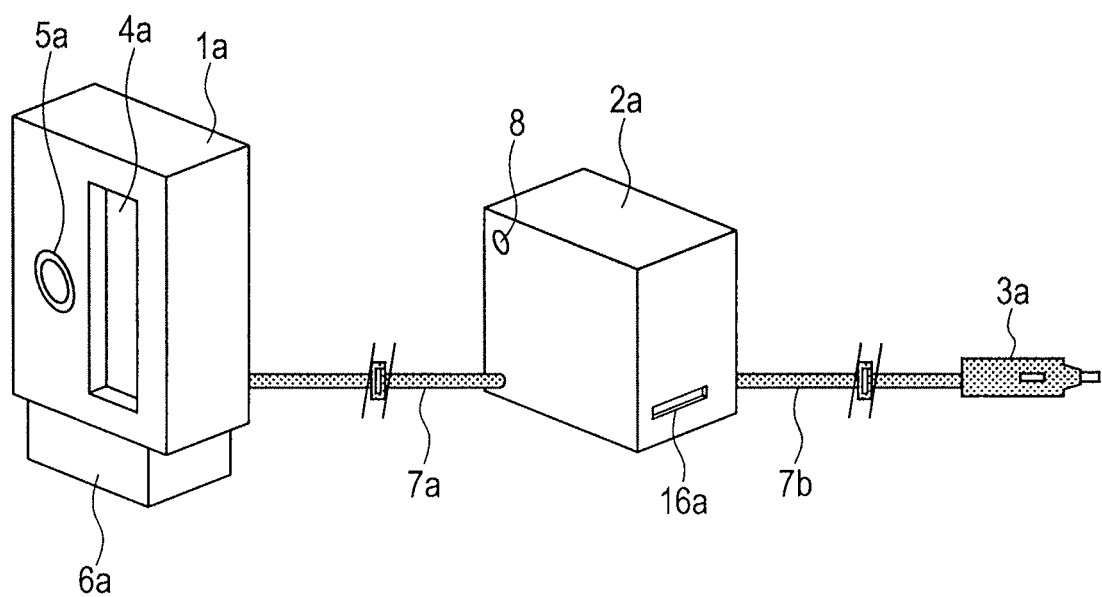
FIG. 1 is a system configuration diagram of a device of the present invention.

An ion detecting portion is allowed to operate under atmospheric pressure, and not only the force by an electric field but also the action of the air resistance, buoyant force, and the force of gravitation that are characteristic when being operated under atmospheric pressure is used as the force acting on ions, so that the following embodiment provides an example of an analyzing method in which ions are separated by a method different from a conventional technique.

Further, in order to provide a analyzing method in which the force by an electric field and the action by the force of gravitation for ions are effectively used, it is also effective to separate ions by applying the force by an electric field in a direction different from the force of gravitation (for example, the direction of the force of gravitation is different from the force by an electric field by 90 degrees). Furthermore, in the case of detecting ions by operating under atmospheric pressure, plural detecting units with the same structure are arranged to be able to easily improve the detection sensitivity. It should be noted that an ammeter that is operated under atmospheric pressure is used for ion detection.

In a conventional mass spectrometer, it is necessary to introduce a sample after reaching a certain vacuum level. However, measurement can be started by introducing a sample immediately after the power is turned on in a device operated under atmospheric pressure.

As described above, if ambient air can be detected with a simple method, breath detection can be realized even in a spatially-restricted place. For example, anti-drunk-driving based on a breath alcohol test can be realized in an automobile.

Further, a mental activity status in the brain can be considered as an internal expression (image). It is conceivable that such an internal expression (image) of mental emotional information in the brain is externally expressed (external expression of emotional information) through gestures, voice, and the like in addition to language. Breathing is considered as one of them, and an interest (value judgment of the brain) in videos, music, and the like can be indirectly measured by detecting a change in breathing.

The embodiment shows an example of detecting ambient air in a noncontact and non-invasive manner. Specifically, an example of detecting breath will be described in detail. Breath is exemplified in the embodiment. However, it is obvious that the embodiment is not limited to breath, but ambient air can be introduced for detection.

Breath contains water of the saturated vapor pressure level at about 37° C. Thus, water in breath is substantially discharged as water clusters to the outside of the body. At this time, water clusters with positive and negative electric charges can be separated by an electric field.

At this time, if high voltage is applied to one voltage applying electrode and water clusters in breath are introduced into a parallel plate electrode in which a detection electrode facing the voltage applying electrode is connected to an ammeter, only clusters with the same polarity as the applied voltage are deflected by an electric field and trapped by the detection electrode, so that current is detected. Specifically, if positive voltage is applied to the voltage applying electrode, water clusters with positive electric charges are trapped by the detection electrode and positive current is detected. On the other hand, if negative voltage is applied to the voltage applying electrode, water clusters with negative electric charges are trapped by the detection electrode and negative current is detected. Breath can be indirectly measured by measuring time changes of the current.

If the entire amount of current is measured in the clusters of normal breath, the amount of current is nearly 0. Thus, it is conceivable that the number of water clusters with positive electric charges is substantially the same as that of water clusters with negative electric charges in breath.

The measurement device includes, in a casing, an inlet through which ambient air is introduced into the casing, a detection electrode that detects part of deflected charged-particles contained in the ambient air introduced into the casing through the inlet, and a voltage applying electrode. The detection electrode and the voltage applying electrode are arranged in parallel, and an electrode holding unit holding the detection electrode and the voltage applying electrode is provided.

Further, a concrete configuration example of detecting alcohol as a detecting system is shown in FIG. 1. A sensor unit 1a includes a sample inlet 4a for introducing breath, an alcohol sensor head (semiconductor sensor or the like) for detecting alcohol, and an air fan unit 6a for discharging part of the introduced breath to the outside of the sensor unit. A small-sized DC fan can be used as the air fan unit 6a. An obtained signal is transmitted to a measurement control system 2a through a cable 7a. The measurement control system includes an indicator lamp 8 for indicating that the system is being operated, and a memory card slot 16a into which a memory card for storing obtained data is inserted. As examples of storage devices, the memory card and the memory card slot 16a are shown in the embodiment. However, it is obvious that the storage devices are not limited to those, but may be external storage media or built-in storage devices.

Power-supply voltage is supplied to the sensor unit 1a and the measurement control system 2a through a cable 7b. For an automobile, power-supply voltage is supplied through a power inverter 3a. A normal household power source or battery can be also used.

Figure 2A:
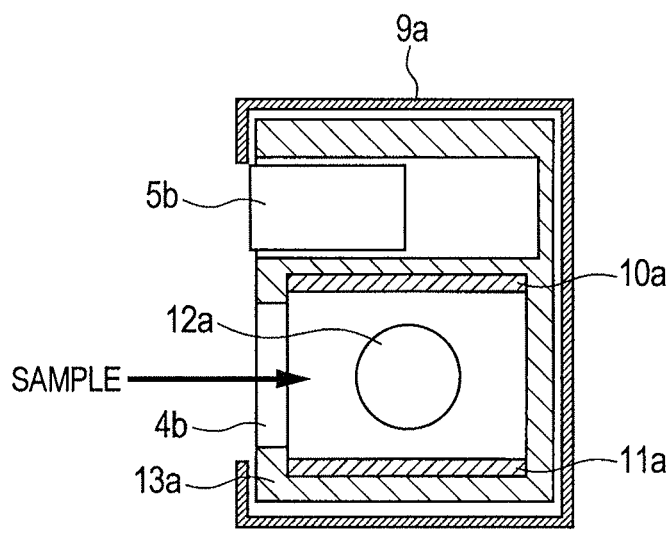
FIG. 2A is a diagram obtained by viewing the inside of a sensor unit of the present invention from the upper side.
Figure 2B:
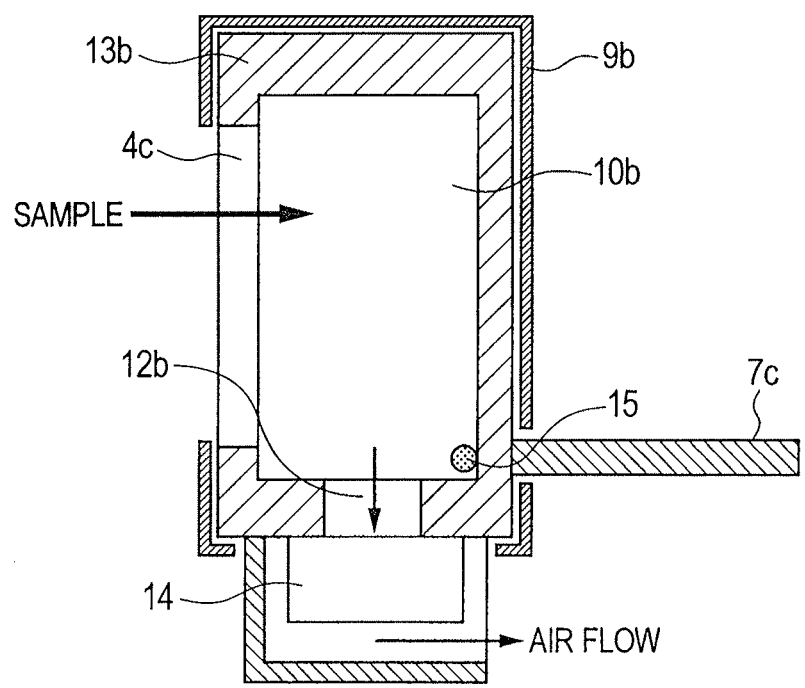
FIG. 2B is a diagram obtained by viewing the inside of the sensor unit of the present invention from one side.

An inner structure of the sensor unit as a detecting device is shown in each of FIG. 2A and FIG. 2B. FIG. 2A is a diagram obtained by viewing the inside of the sensor unit from the upper side, and FIG. 2B is a diagram obtained by viewing the inside of the sensor unit from one side. As shown in FIG. 2A, breath introduced from a sample inlet 4b is introduced into a space sandwiched between a voltage applying electrode 10a and a detection electrode 11a held by an electrode holding unit 13a. Voltage is applied to the voltage applying electrode and current is detected by the detection electrode. Thus, the electrode holding unit 13a is an insulating member. The sample introduction direction is closed at the electrode holding unit 13a, and part of breath is discharged from an air port 12a to the outside of the system. An alcohol sensor head 5b for detecting alcohol is arranged adjacent to the voltage applying electrode 10a. On the other hand, as shown in FIG. 2B, the breath introduced from a sample inlet 4c hits a wall of an electrode holding unit 13b and moves downward. Then, part of the breath is discharged from an air port 12b to the outside of the system through an air fan 14. Although the air fan 14 is exemplified in the embodiment, the fan is not necessarily provided. It is possible to inhale the breath from outside.

Figure 3A:
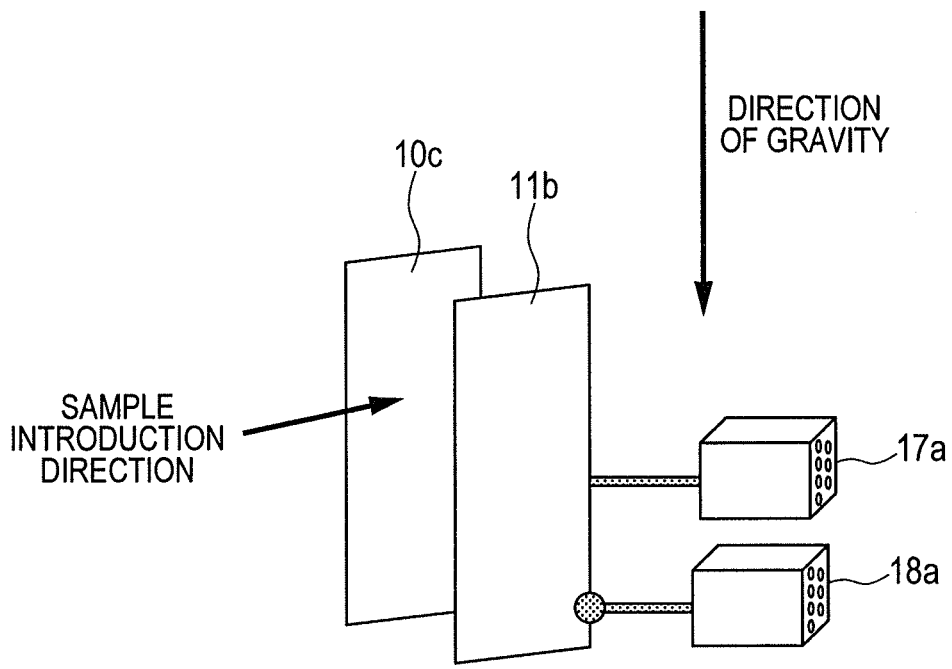
FIG. 3A is a diagram for showing a detection principle in the device of the present invention.
Figure 3B:
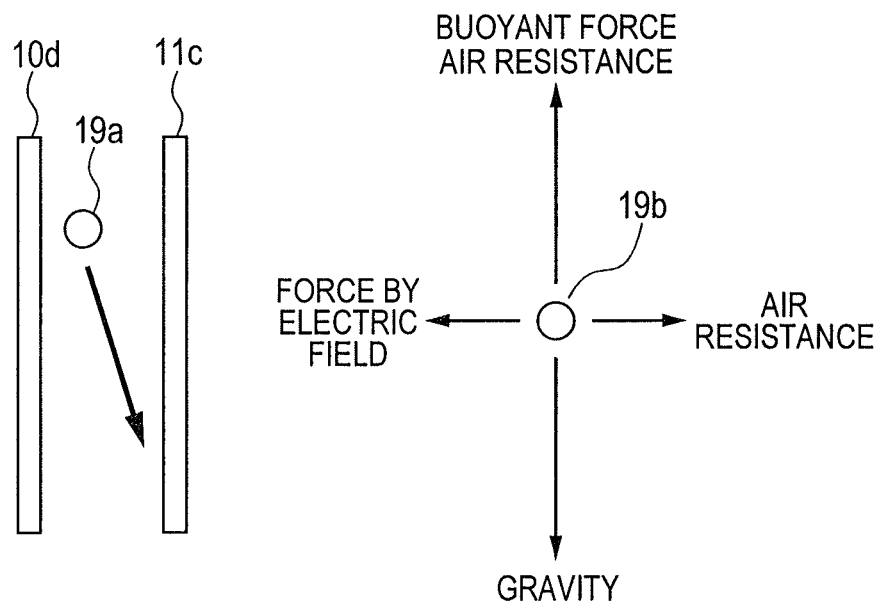
FIG. 3B is a diagram for showing a detection principle in the device of the present invention.

A detection principle of the present invention is shown in each of FIG. 3A and FIG. 3B. A potential difference is provided between a voltage applying electrode 10c and a detection electrode 11b by a sensor power source 17a. In this case, if breath containing water clusters is introduced into a space sandwiched between the voltage applying electrode 10c and the detection electrode 11b from the arrow direction, the forces by the air resistance, buoyant force, force of gravitation, and an electric field act on a small charged water cluster 19b as shown in FIG. 3B. If positive voltage is applied to a voltage applying electrode 10d, only a water cluster having a positive electric charge is deflected due to the relation of these forces to hit a detection electrode 11c and positive current is detected. On the other hand, if negative voltage is applied to the voltage applying electrode 10d, only a water cluster having a negative electric charge is deflected to hit the detection electrode 11c and negative current is detected. Accordingly, it is a small charged water cluster 19a that is deflected to hit the detection electrode 11c, and a large charged water cluster is not detected because it does not hit the detection electrode 11c. As described above, the direction of the force of gravitation is important in the present invention, and thus it is vital that ambient air such as breath can pass through a space formed between the voltage applying electrode 10d and the detection electrode 11c towards the direction of the force of gravitation.

Further, it is preferable that the voltage applying electrode 10d and the detection electrode 11c are arranged along the direction of the force of gravitation. It is more preferable that the voltage applying electrode 10d and the detection electrode 11c are arranged substantially in parallel with the direction of the force of gravitation.

In order to understand the above-described process, it is necessary to analyze the motion of a water cluster having an electric charge in the direction of the force of gravitation and the motion thereof in the direction orthogonal to the direction of the force of gravitation. In the first place, the motion of a water cluster having an electric charge in the direction of the force of gravitation will be analyzed.

Stokes found that the air resistance acting on a small water cluster is proportional to the radius r of a sphere and the velocity $v_g$ of the sphere in the direction of the force of gravitation. The magnitude of the air resistance is represented by the following equation using the rate of viscosity $\eta$ of air.

The magnitude of air resistance=$6\pi\eta r v_g$

Further, the magnitude of buoyant force by the air is equal to the force of gravitation acting on the air removed by the object. Thus, in the case of a sphere with a radius of r, the magnitude of buoyant force by the air is equal to $(4/3)\pi r^3 \rho_f g$ in which the density of the air is $\rho_f$, and the acceleration of gravity is g. Thus, the motion equation acting in the direction of the force of gravitation by a water cluster with a mass of m is represented as $$m \cdot (dv_g/dt) = (4/3)\pi r^3 \rho_p g - 6\pi\eta r v_g - (4/3)\pi r^3 \rho_f g$$

in which $\rho_p$ is the density of water. In the case of a droplet falling in the air at 25° C. under an atmospheric pressure of 1, the density of water $\rho_p$=997.04 kg/m$^3$, the density of the air $\rho_f$=1.1843 kg/m$^3$, the rate of viscosity of the air $\eta$ (25° C.)=0.0000182, and the acceleration of gravity g=9.807 m/s$^2$. If $v_g$ is positive, the acceleration becomes 0 with the lapse of time, and water clusters in the air uniformly move at a constant velocity. The final velocity $v_{g0}$ of the velocity is represented as the following equation by assigning 0 to the above equation.

$$v_{g0} = 2r^2(\rho_p - \rho_f)g/(9\eta)$$

Next, the motion of a water cluster having an electric charge in the direction orthogonal to the direction of the force of gravitation will be analyzed. If it is assumed that the electric charge of a water cluster is q and the magnitude of an electric field is E, the motion equation when the water cluster having an electric charge is moved in the direction orthogonal to the direction of the force of gravitation is represented as the following equation.

$$m \cdot (dv_t/dt) = qE - 6\pi\eta r v_t$$

Thus, the final velocity $v_{t0}$ at this time is represented as $v_{t0}$=qE/($6\pi\eta r$). In this case, the electric charge q=1.6021×10$^-$ 19 C(A·s). The electric field E is 100000 V/m if, for example, 1000 V is applied between the voltage applying electrode and the detection electrode that are part from each other by 10 mm.

Here, for a water cluster in the air at 25° C. under an atmospheric pressure of 1, a measurement result and a calculation result are compared with each other using the density of water $\rho_p$=997.04 kg/m$^3$, the density of the air $\rho_f$=1.1843 kg/m$^3$, the rate of viscosity of the air $\eta$=0.0000182, the acceleration of gravity g=9.807 m/s$^2$, the electric charge q=1.6021×10$^{-19}$ C(A·s), and the electric field E=100000 V/m.

Figure 4A:
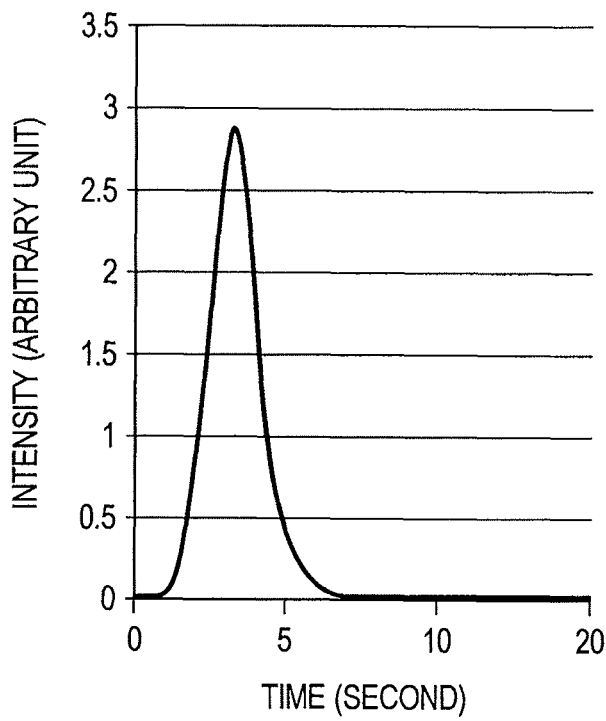
FIG. 4A is a diagram for showing a detection result in the device of the present invention.
Figure 4B:
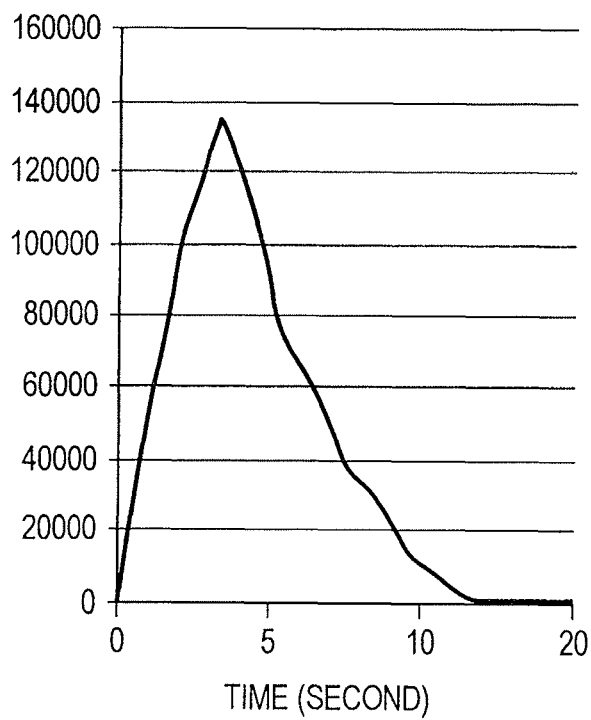
FIG. 4B is a diagram for showing a calculation result in the device of the present invention.

FIG. 4A shows a measurement result by the present invention for one breath in the case of an expiration time of about 3 seconds, and FIG. 4B shows a calculation result on the basis of the above-described concept. It is assumed in calculation that when a water cluster with a radius of 0.01 μm to 0.5 μm in breath is introduced into a space sandwiched between the voltage applying electrode and the detection electrode each of which has a length of 50 mm and which are apart from each other by 10 mm, the water cluster is quickly detected while being charged. Further, it is conceivable that if a water cluster having an electric charge hits the detection electrode before passing through the space sandwiched between the both electrodes, the water cluster can be detected. Thus, the measurement result is represented as frequency distribution of times required to reach the detection electrode from plural points existing in the space sandwiched between the both electrodes. The results shown in FIG. 4A and FIG. 4B can mostly explain the reason that breath can be monitored in a few seconds of the full width at half maximum of the peak in the present invention (the full width at half maximum of the peak of the measurement result is about 2 seconds, whereas the full width at half maximum of the peak of the calculation result is about 4 seconds). Further, it is conceivable on the basis of these results that the detectable radius of a water cluster is about 1 μm or smaller.

The current detected by the detection electrode 11*b* is amplified by a sensor amplifier 18*a* to be converted into voltage, and the voltage is transferred to a CPU.

Figure 5:
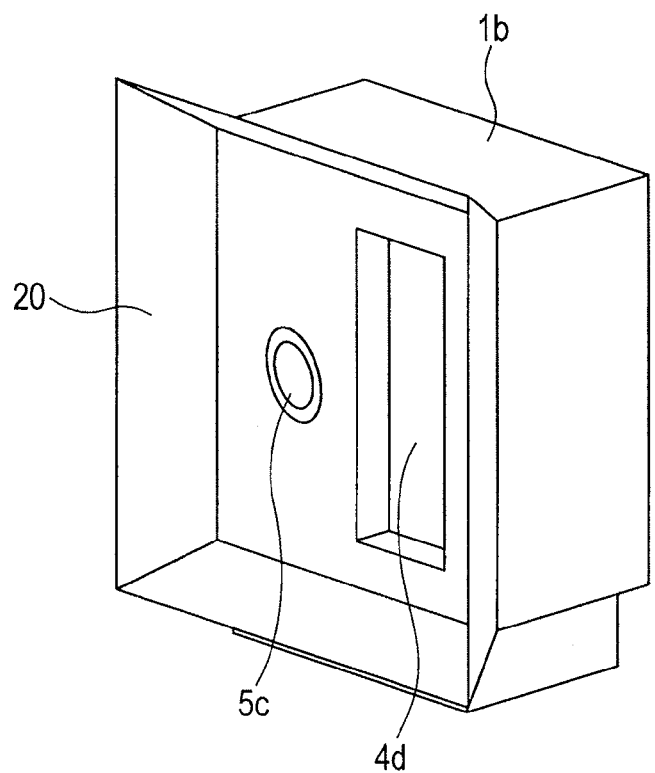
FIG. 5 is an external diagram of a breath sensor unit of the device of the present invention.
Figure 6:
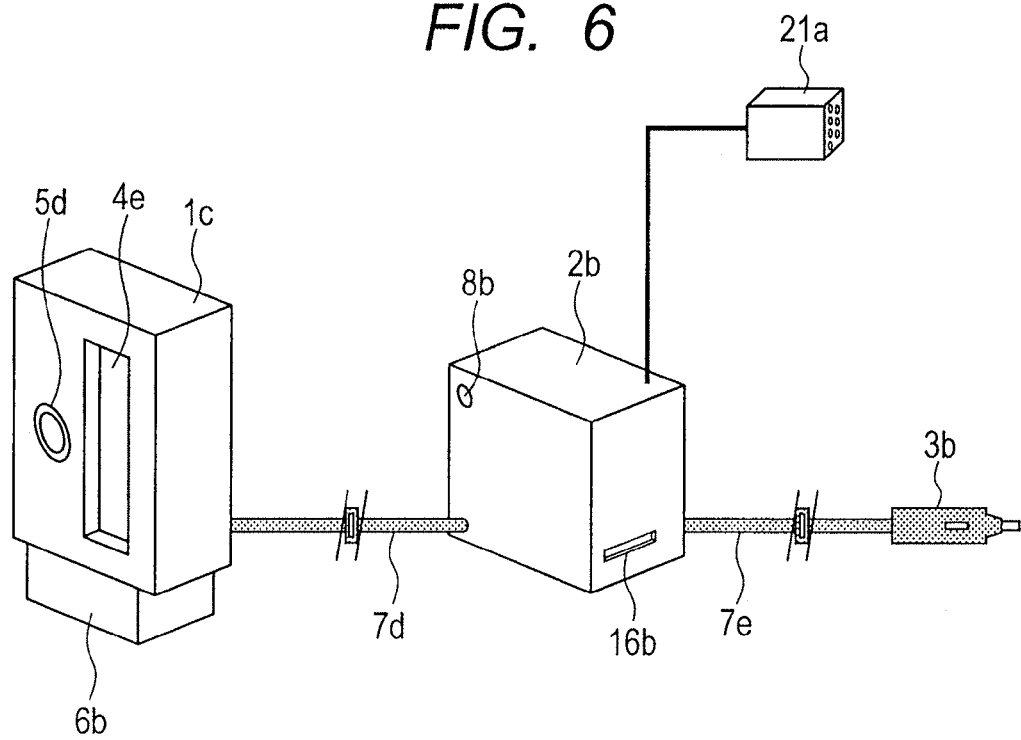
FIG. 6 is a system configuration diagram of the device of the present invention.

Further, it is effective, as shown in FIG. 5, that a flange 20 is provided at a sensor unit 1*b* so as to easily introduce breath into the sample inlet 4*c* and an alcohol sensor head 5*c*. Furthermore, it is effective, as shown in FIG. 6, that in addition to the system shown in FIG. 1, a GPS antenna 21*a* is provided to obtain position information of a moving object.

Figure 7:
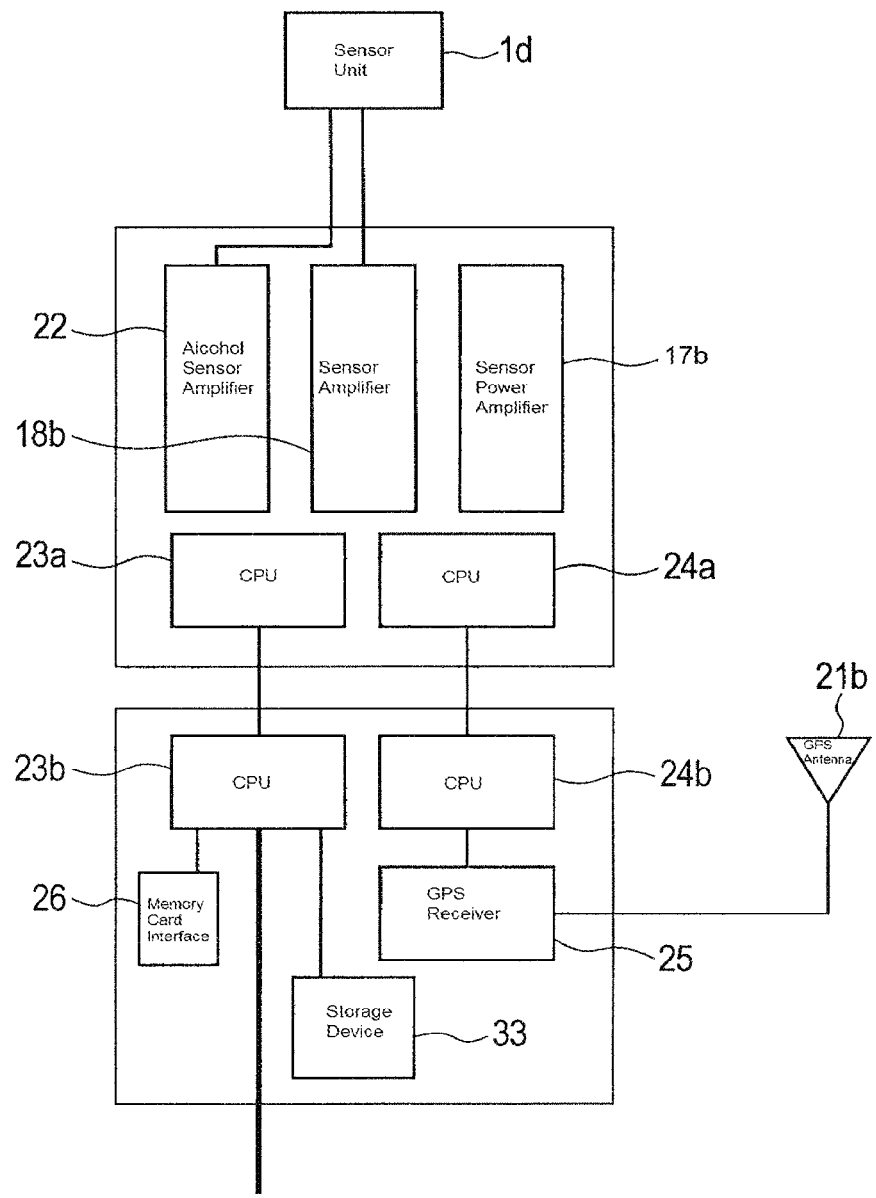
FIG. 7 is a circuit configuration diagram of the device of the present invention.
Figure 8:
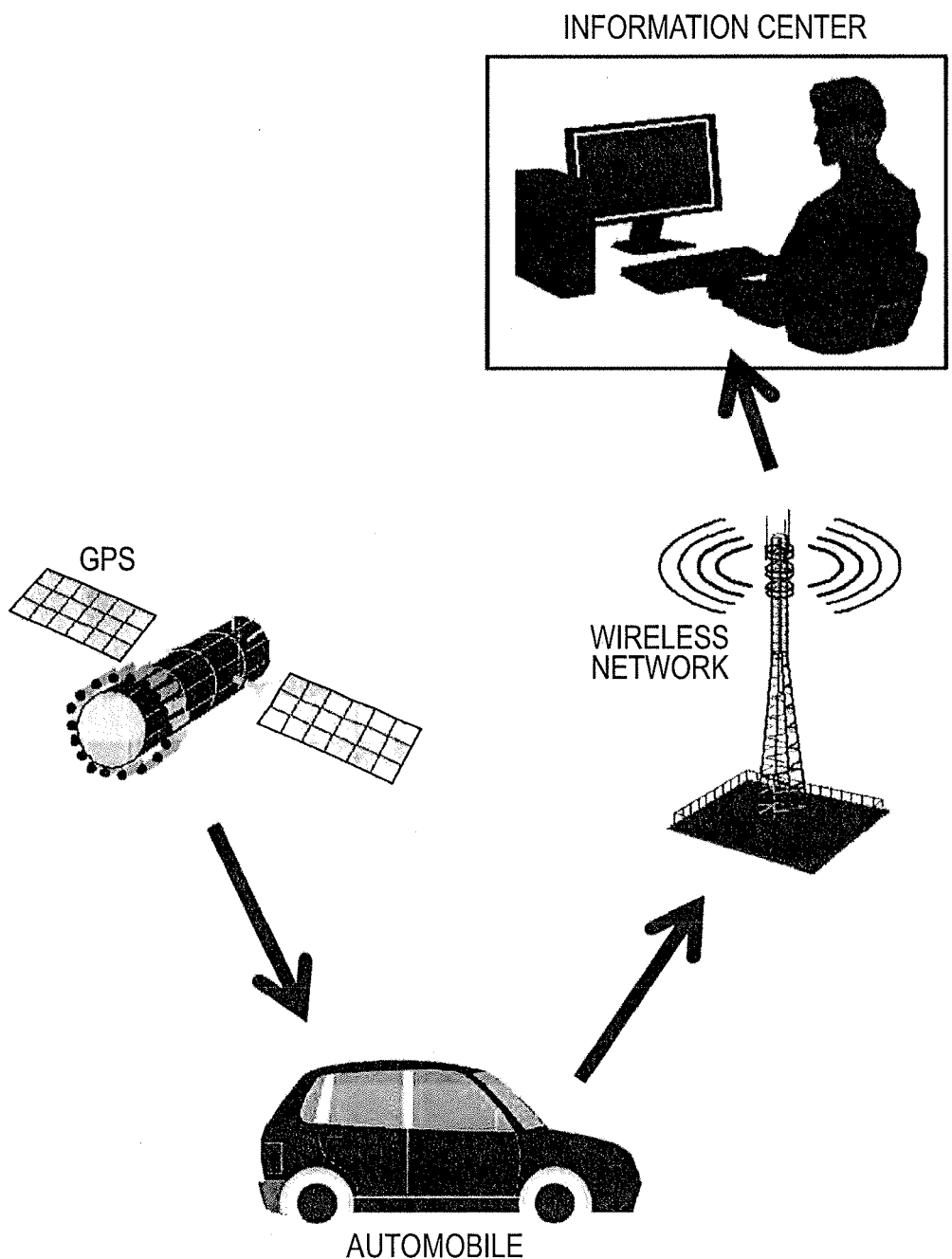
FIG. 8 is a diagram for showing a usage instance of the device of the present invention.

A circuit configuration of a sensor is shown in FIG. 7. Voltage is supplied from a sensor power source 17*b* to a sensor unit 1*d*, the signal of breath obtained by the sensor unit 1*d* is amplified by a sensor amplifier 18*b* to be converted into voltage, and the voltage is transferred to a CPU 23*a*. Likewise, the signal of alcohol detected by an alcohol sensor head is amplified by an alcohol sensor amplifier 22 to be transferred to the CPU 23*a*. Further, position information obtained by a GPS antenna 21*b* and a GPS receiver 25 is transferred to a CPU 23*b*. Information such as the signal of breath, the signal of alcohol, position information, and time information (an inner timer is corrected by obtaining from a GPS signal) is finally obtained, and is stored in a storage device. As a concrete example, the information is accumulated into a memory card through a memory card interface 26. FIG. 8 shows a case in which information obtained from a wireless network is transmitted to an information center. However, it is effective to make use of such information.

Figure 9:
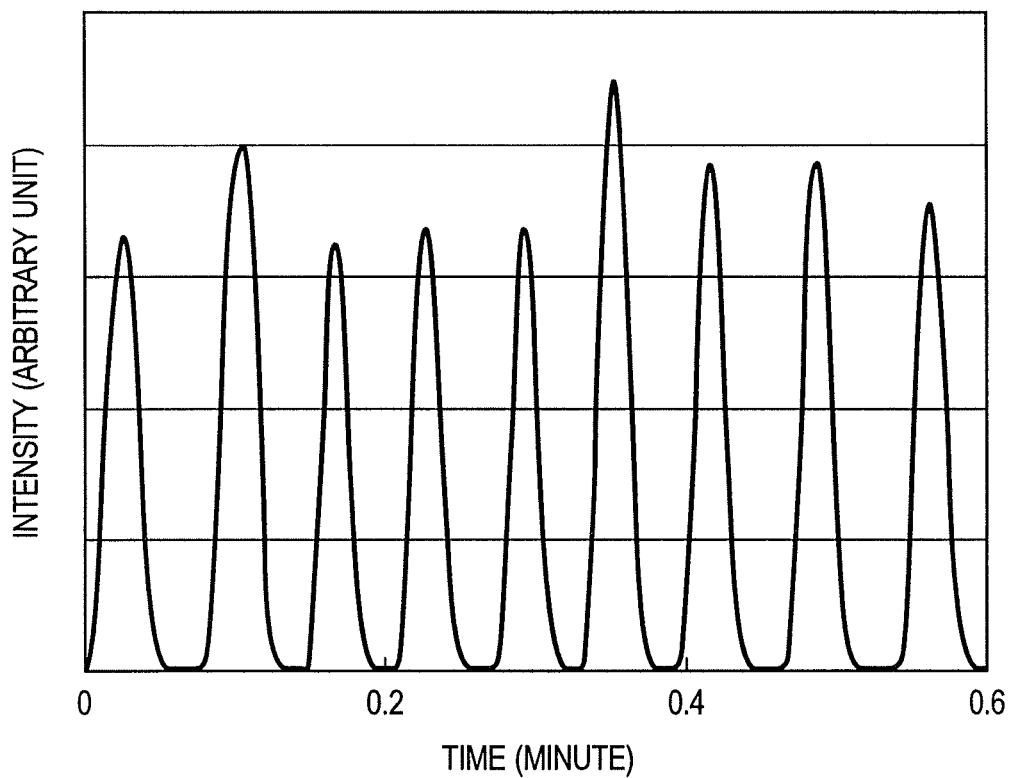
FIG. 9 is a diagram for showing an example of continuously detecting breath in the device of the present invention.

FIG. 9 shows an example in which nose breathing of a person was continuously measured using the system shown in FIG. 1. It can be found that one breath peak corresponds to one breath, and the resolution of one breathing is provided. Incidentally, there is an important point to obtain such data with a good S/N ratio.

Figure 10:
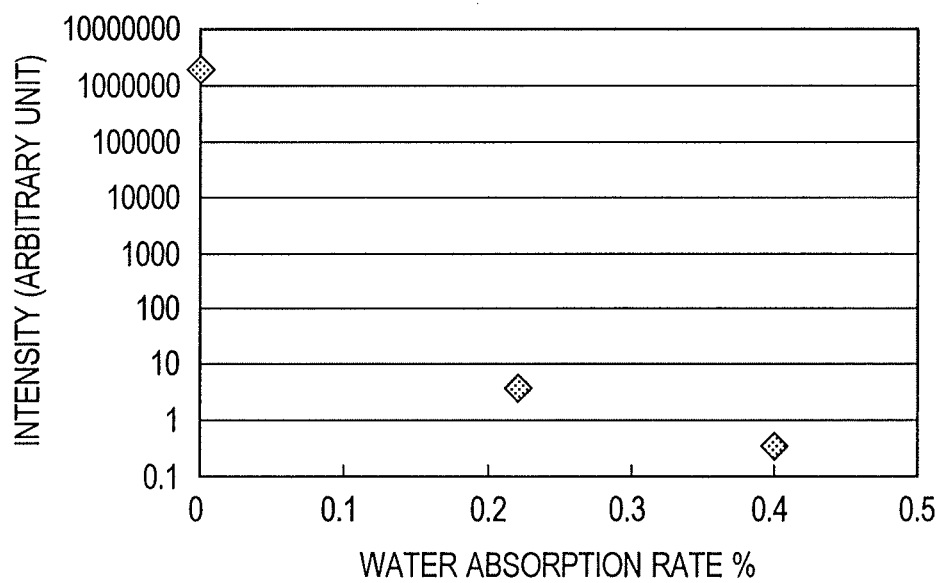
FIG. 10 is a diagram for showing the dependency of breath peak intensities on the water absorption rates of materials in the device of the present invention.

FIG. 10 shows a difference in the signal intensities of breath peaks due to different materials for the electrode holding unit 13*a* shown in FIG. 2.

The voltage applying electrode 10*a* and the detection electrode 11*a* need to be made of metal such as stainless steel. The material of the electrode holding member 13*a* that is arranged around the voltage applying electrode 10*a* and the detection electrode 11*a* and that is exposed to water clusters is highly important.

If a water-absorbing material is used for a device that detects a water cluster with a small diameter, the water cluster is absorbed by the member and the number of water clusters involved in detection is reduced. Thus, the sensitivity of detection is considerably reduced. FIG. 10 shows a plot diagram in which the horizontal axis represents the water absorption rates of materials and the vertical axis represents the intensities of breath peaks. FIG. 10 shows a result in which breath peaks were measured using a member with a water absorption rate of 0 such as ceramic that can be cut, a material with a water absorption rate of about 0.25 such as polyacetal, and a material with a water absorption rate of about 0.4 such as polyvinyl chloride for the electrode holding member. Specifically, a little breath peak is detected with a water absorption rate of about 0.4, whereas a breath peak is beginning to be definitely detected with a water absorption rate of about 0.25. On the other hand, in the case of a water absorption rate of 0, the intensity of a breath peak is increased by 6 digits or more as compared to the case with a water absorption rate of 0.4. This means that the material of the electrode holding member exposed to water clusters is highly important in the present invention.

Thus, it is necessary to use a material with a water absorption rate of 0 or larger and 0.4 or smaller for the electrode holding material. It is preferable to use a material with a water absorption rate of 0 or larger and 0.25 or smaller. Further, even if a material with a water absorption rate of larger than 0.4 is used, a peak can be detected by adjusting the sensitivity. However, there is a possibility that the result is likely to contain noise.

Figure 11:
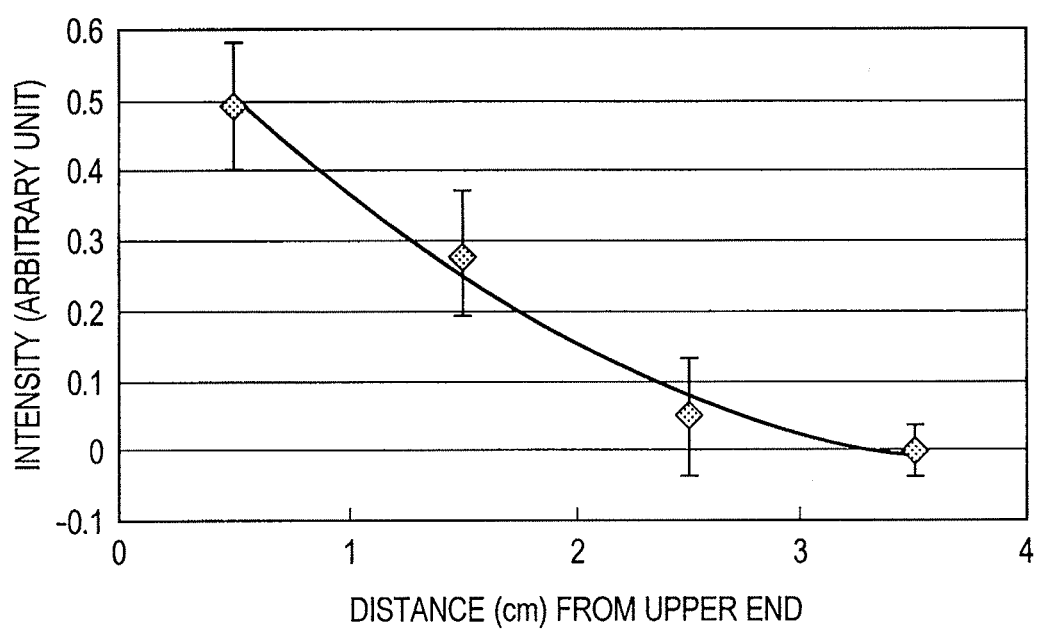
FIG. 11 is a diagram for showing the dependency of breath on introduction positions in the device of the present invention.

On the other hand, FIG. 11 shows the dependency of the breath peak intensity on the breath introduction position in the sample inlet 4*a* shown in FIG. 1. FIG. 11 shows changes in the breath peak intensity in the case where the center of a silicon tube having an inner diameter of 10 mm is arranged at positions apart from an end of an opening portion (4 cm H by 0.6 cm W) by 0.5 cm, 1.5 cm, 2.5 cm, and 3.5 cm. It is apparent that the breath peak intensity becomes stronger on the upper side where it takes time for water clusters to move. However, the result shows that the breath peak intensity can be sufficiently measured at a position of 2.5 cm. The information is important in downsizing the sensor unit. In addition, the result shows that in the case of an opening portion with a width of about 0.6 cm (the distance between the voltage applying electrode and the detection electrode is about 1 cm), if the length is about 1 cm, the breath peak intensity can be measured. Further, this means that it is only necessary for the voltage applying electrode or the detection electrode to have a length of about 1 cm in the direction of the force of gravitation. Specifically, if the voltage applying electrode and the detection electrode are arranged substantially in parallel with the direction of the force of gravitation and if the distance between the both electrodes is about 10 mm and the length of each in the direction of the force of gravitation is about 10 mm, breath can be sufficiently detected. In other words, if the opening portion as a space into which breath is introduced has about 10 mm×10 mm in size, it can be said that the size is sufficient in detection of breath.

On the contrary, if a sensor having an opening portion that is longer in the vertical direction (specifically, the voltage applying electrode and the detection electrode that are longer in the direction of the force of gravitation) is used, the sensitivity is further improved. Further, widening the width between the both electrodes in the direction orthogonal to the direction of the force of gravitation is obviously effective in improving the sensitivity.

Second Embodiment

The present invention can be used for a breath alcohol sensor in a mobile object such as an automobile. If the alcohol sensor head 5a such as a semiconductor sensor is used, the sensor unit 1a and the alcohol sensor unit can be easily integrated as shown in FIG. 1. In addition, breath and alcohol can be simultaneously measured. In the case where the device is mounted in an automobile or the like, the measurement can be conducted by breathing into the device fixed on the column cover placed behind the steering wheel or by breathing into the sensor unit that is removable.

Figure 12:
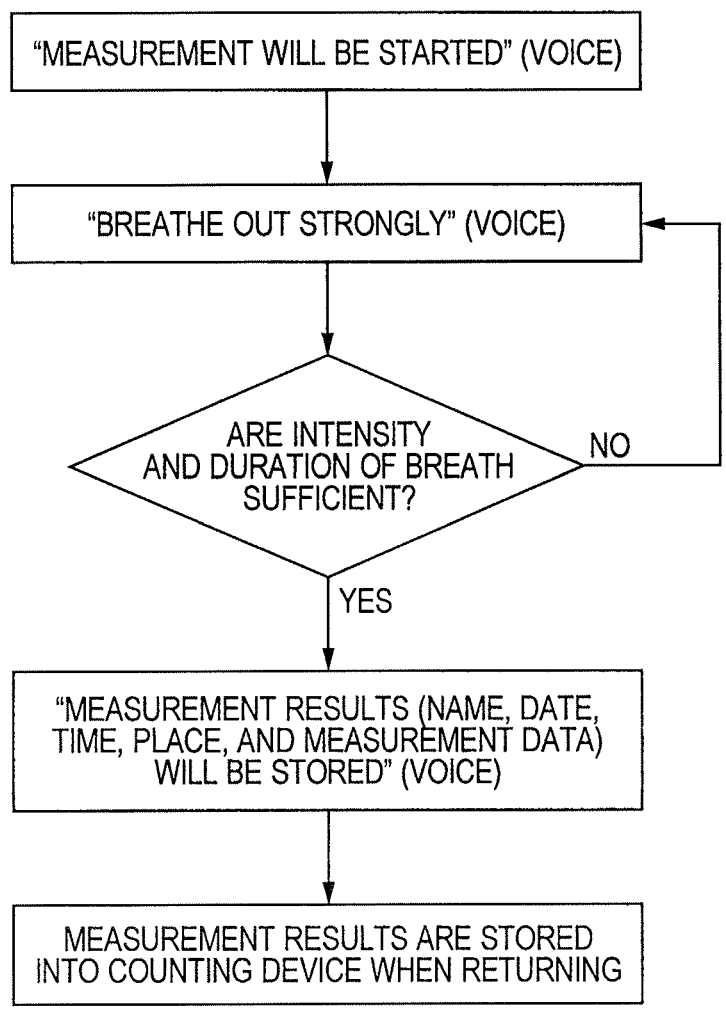
FIG. 12 is a diagram for showing a detection algorithm of breath alcohol in the device of the present invention.

An algorithm of a breathalyzer test in the case where the present invention is used is shown in FIG. 12. For example, after starting the engine, a driver immediately breathes out into the sensor unit 1a for a few seconds in accordance with the voice guidance. Threshold values of the intensity and duration for detection of breath peaks are provided. When not exceeding the values, the driver breathes again. If the breath peak intensity and duration are sufficient, breath and alcohol are simultaneously measured. The measurement results such as the information of the name, the date of measurement, time, and place are stored in a memory card or the like. It is effective to store the measurement results into another counting device. Accordingly, it is possible to manage the history of drunk driving. Further, when alcohol (ethanol) is detected, it is also effective to determine whether or not the timing of detection of the breath peak matches the timing of detection of the alcohol peak. Furthermore, in the case where the sensor unit is fixed on the column cover placed behind the steering wheel, a breathalyzer test can be conducted even during driving or when the car is parked.

Figure 13:
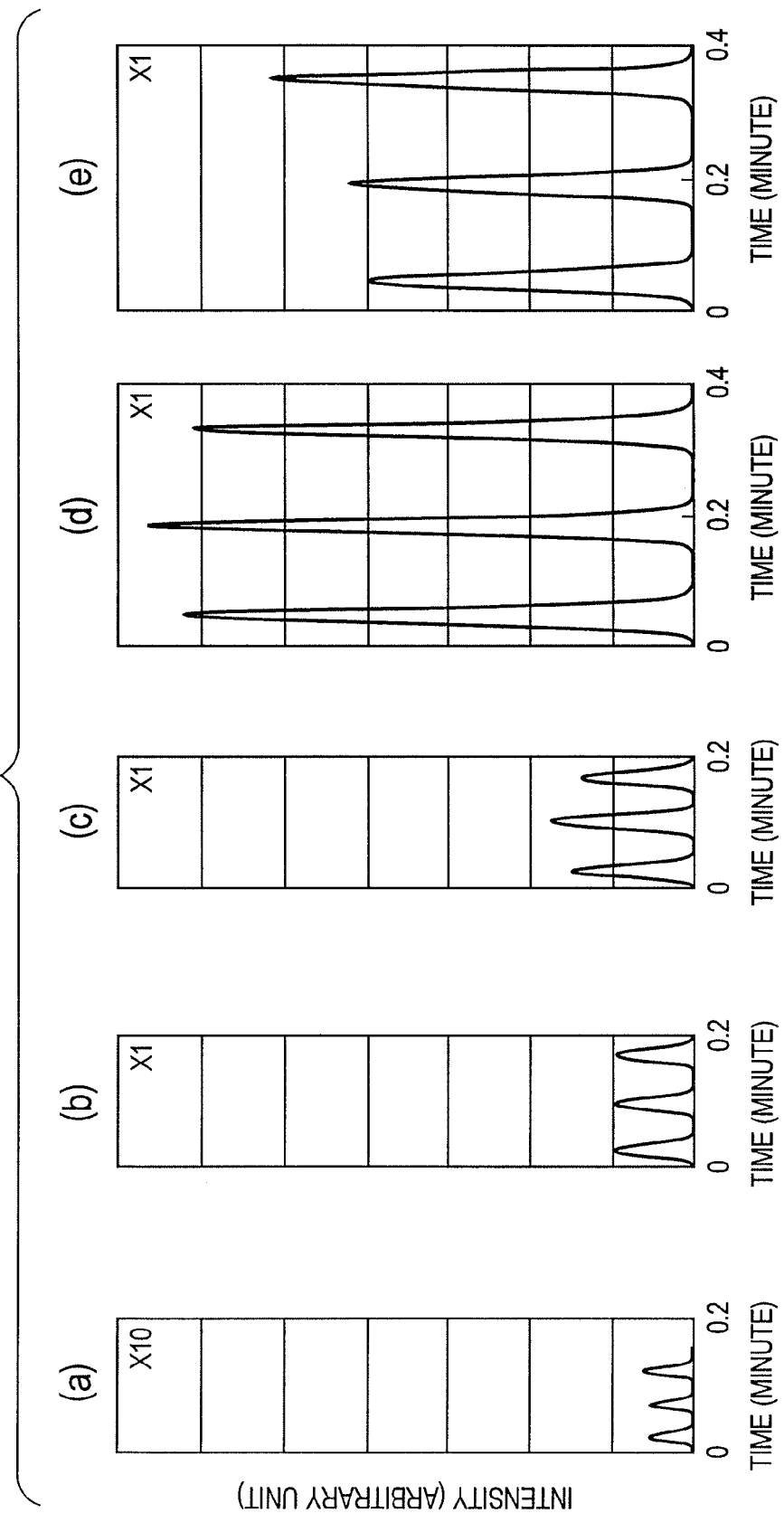
FIG. 13 is a diagram for showing the dependency of breath peak intensities on breathing methods in the device of the present invention.
Figure 14:
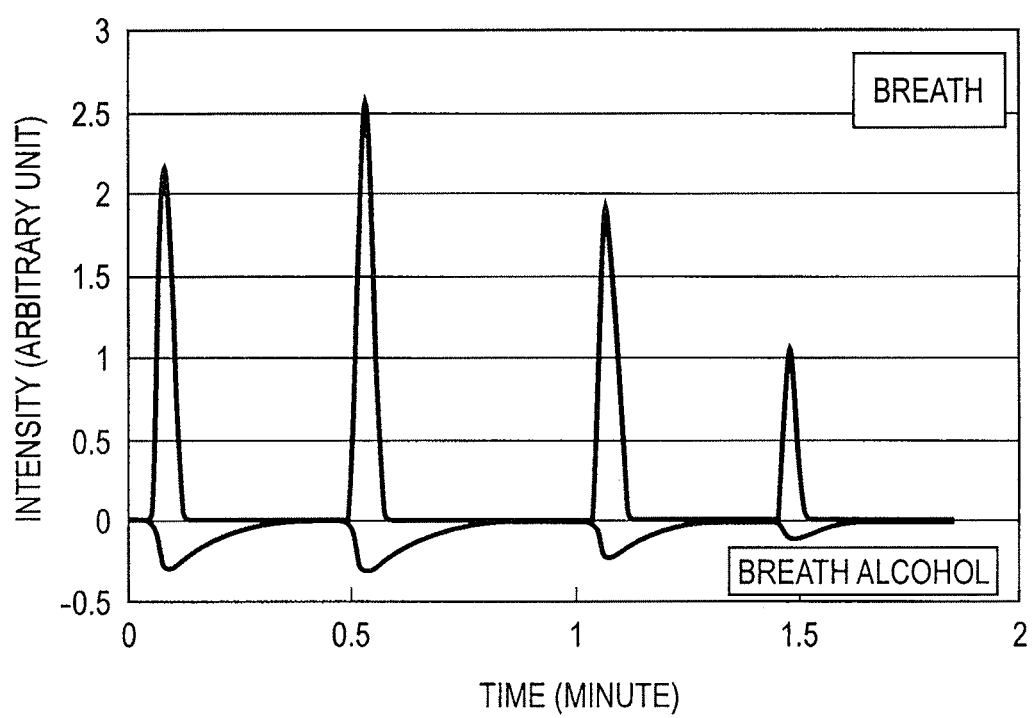
FIG. 14 is a diagram for showing an example of detecting breath alcohol in the device of the present invention.
Figure 15:
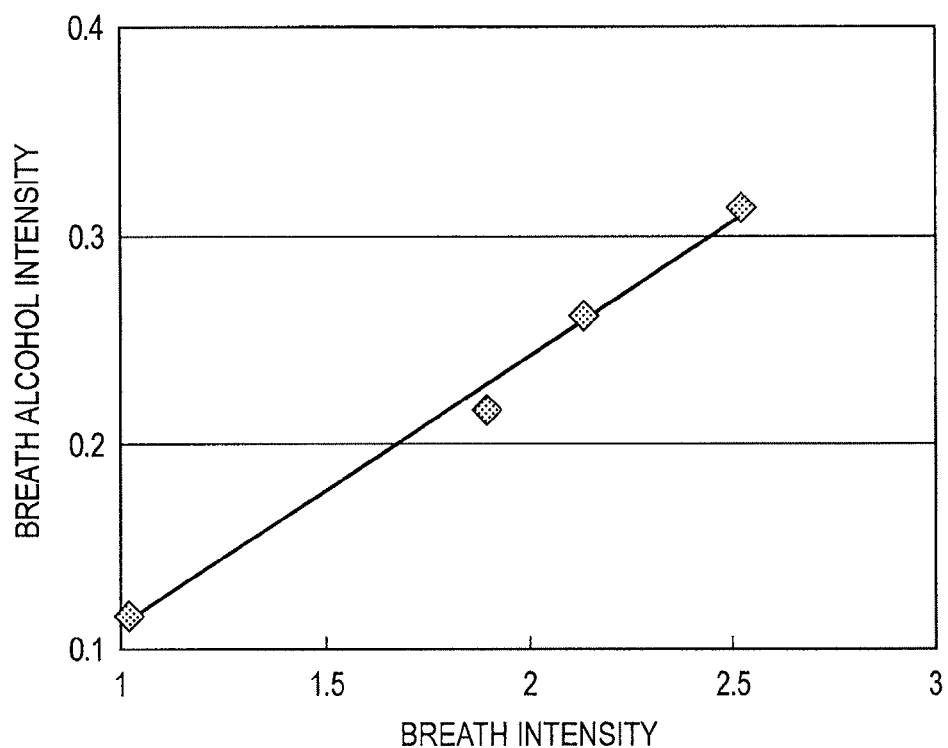
FIG. 15 is a diagram for showing a relation between breath peak intensities and breath alcohol peak intensities in the device of the present invention.

If a breathalyzer test is conducted using the present invention, it is important to fix a breathing method to secure quantitation. FIG. 13 shows changes in the breath peak intensity due to different breathing methods. In FIG. 13, (a) shows a case of normal breathing (measured three times), (b) shows a case of chest respiration (measured three times with an expiration time of about one second), (c) shows a case of abdominal respiration (measured three times with an expiration time of about one second), (d) shows a case of chest respiration (measured three times with an expiration time of about three seconds), and (e) shows a case of abdominal respiration (measured three times with an expiration time of about three seconds). In this case, the measurement was conducted while keeping the distance between the nose and the sample inlet of the sensor unit constant. The breath peak intensity differs by about two digits depending on breathing methods. If the breath peak intensity can be detected at least as the case of chest respiration (measured three times with an expiration time of about one second) or the case of abdominal respiration (measured three times with an expiration time of about one second), it is very difficult to show the amount of breath alcohol considerably smaller than the actual amount. FIG. 14 shows a detection example of breath alcohol in conjunction with breathing. If the expiration time differs even in the same abdominal respiration, both of the breath peak and the alcohol peak intensity differ. To easily distinguish between the breath peak and the alcohol peak, the output of the alcohol peak is inverted in this figure. FIG. 15 shows a correlation between breath peaks and alcohol peak intensities. The result shows that if the breath peak is correctly measured (at a certain intensity or higher and at a certain duration or longer), it is difficult to show the amount of breath alcohol smaller than the actual amount. Further, if the relational equation between breath peak intensities and breath alcohol peak intensities is used, the breath alcohol intensity can be corrected with the breath peak intensity. Accordingly, it becomes more difficult to show the amount of breath alcohol smaller than the actual amount. It should be noted that FIG. 15 shows data obtained when 30 minutes passed after drinking 200 ml of wine with an alcohol concentration of 10% (the value of the breath alcohol concentration measured with a high-accuracy alcohol sensor was 0.10 mg/L).

Figure 16:
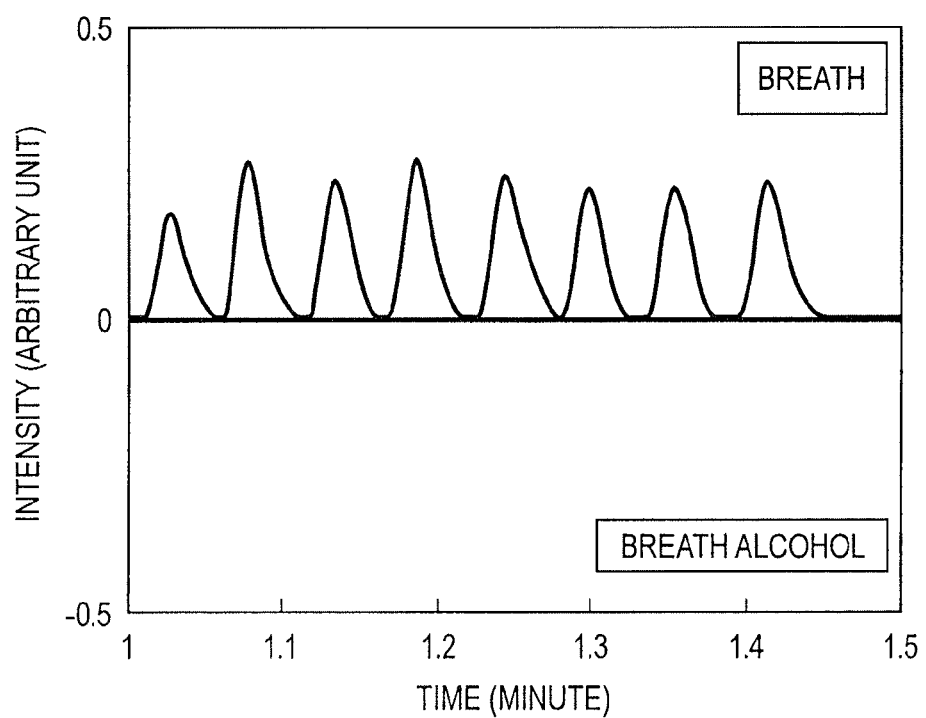
FIG. 16 is a diagram for showing an example of detecting breath peaks and breath alcohol peaks in the device of the present invention in the case of a person who drank no alcohol.
Figure 17:
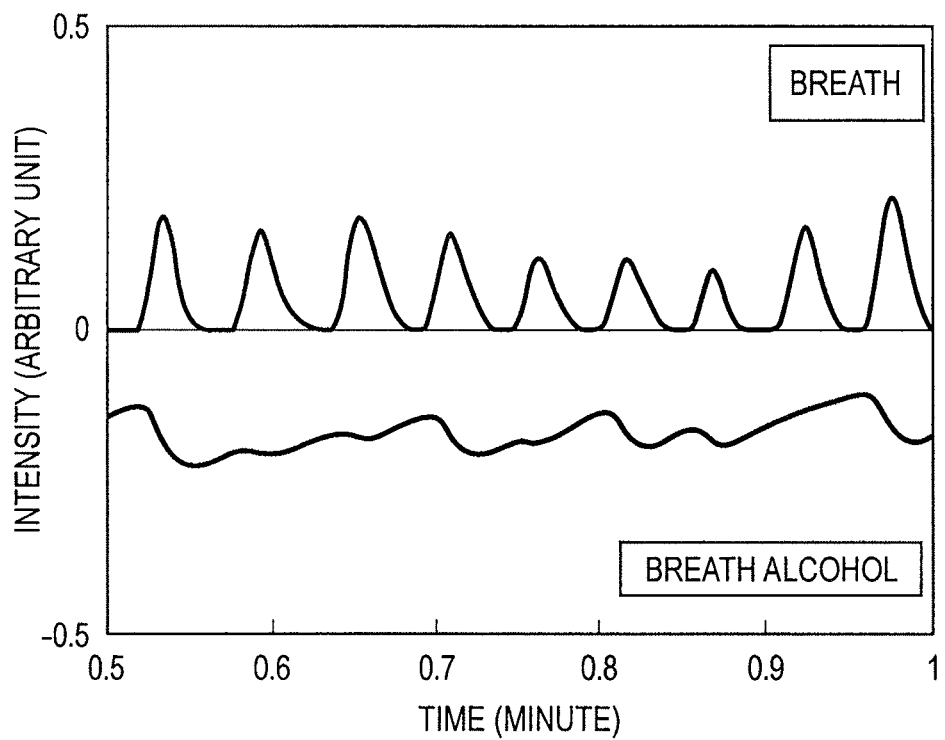
FIG. 17 is a diagram for showing an example of detecting breath peaks and breath alcohol peaks in the device of the present invention in the case of a person who drank alcohol.

Further, a result of detecting breath and breath alcohol when breathing was continuously measured is shown in each of FIG. 16 and FIG. 17. As shown in FIG. 16, in the case of a person who drank no alcohol, breath was measured, but breath alcohol was not detected. On the other hand, in the case of a person who drank alcohol, alcohol in conjunction with breath peaks was detected as shown in FIG. 17. Further, since the temporal resolution is poor in detection of alcohol using a semiconductor sensor as compared to detection of breath, the peaks appear to be overlapped, which proves to have drunk. To easily distinguish between the breath peak and the alcohol peak, the output of the alcohol peak is inverted in this figure. It should be noted that FIG. 17 shows data obtained when 30 minutes passed after drinking 200 ml of wine with an alcohol concentration of 10% (the value of the breath alcohol concentration measured with a high-accuracy alcohol sensor was 0.10 mg/L).

Third Embodiment

Figure 18:
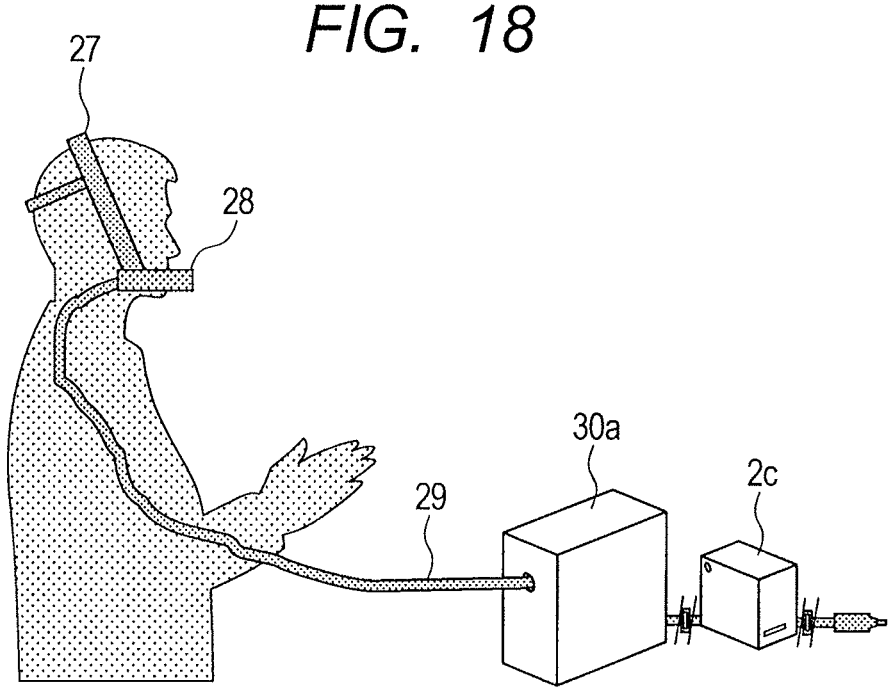
FIG. 18 is a system configuration diagram in the case where a head set is used in the device of the present invention.
Figure 19A:
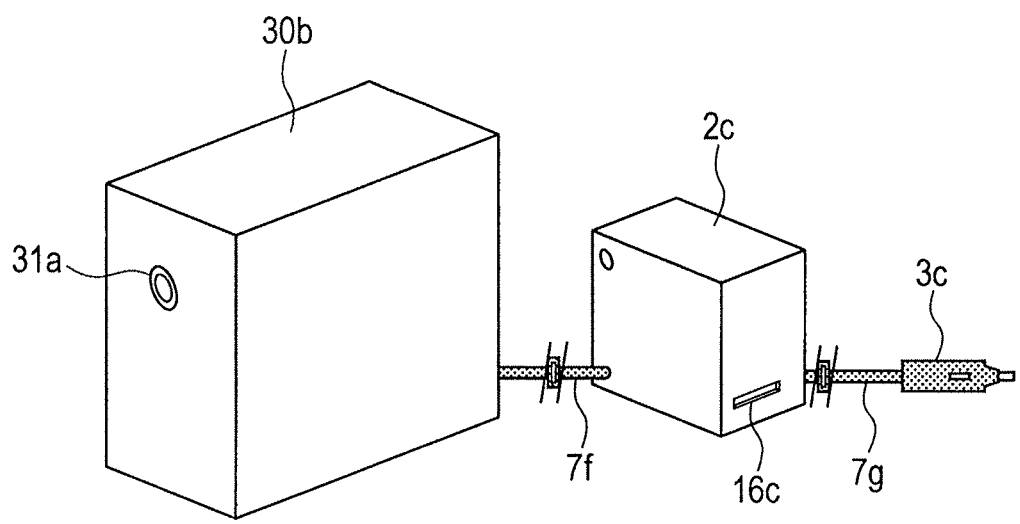
FIG. 19A is a diagram for showing a breath sensor detecting unit in the case where a head set is used in the device of the present invention.
Figure 19B:
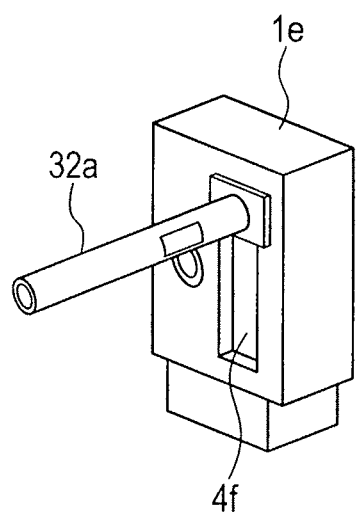
FIG. 19B is a diagram for showing introduction of breath into a sensor unit in FIG. 19A.
Figure 20A:
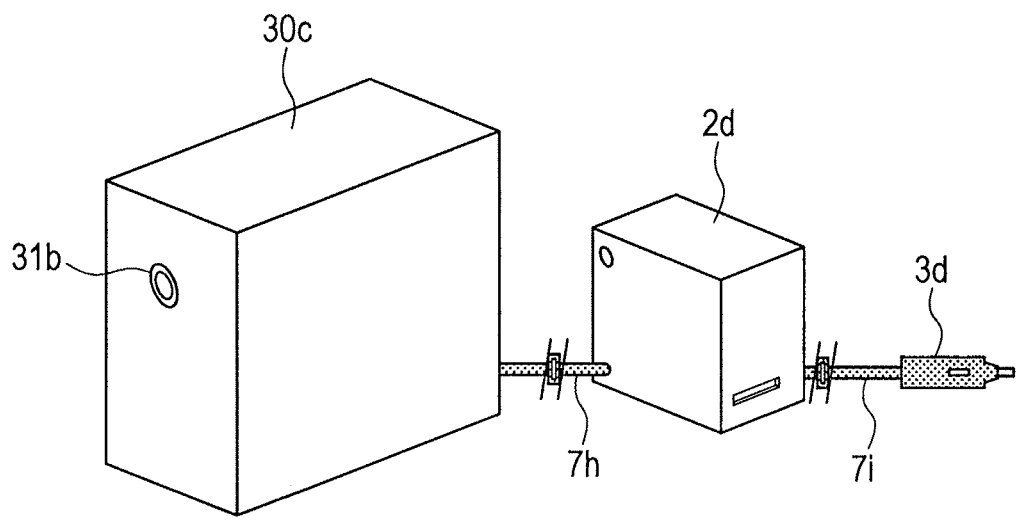
FIG. 20A is a diagram for showing a breath sensor detecting unit in the case where a head set is used in the device of the present invention.
Figure 20B:
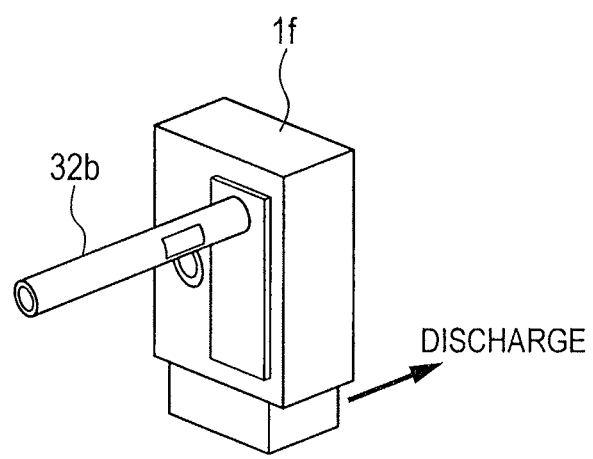
FIG. 20B is a diagram for showing introduction of breath into a sensor unit in FIG. 20A.

As shown in FIG. 18, if only a breath inlet 28 is provided at a head set 27 and the measurement of breathing can be conducted with a head set sensor unit 30a through a transfer tube 29, the application range can be further widened. FIG. 19A shows a structure of a head set sensor unit 30b. Breath introduced from the breath inlet 28 provided at the head set 27 passes through the transfer tube 29 and is fed to a sample introduction pipe 32a through a transfer tube connector 31a as shown in FIG. 19B. A tip end of the sample introduction pipe 32a is placed at an upper portion of a sample inlet 4e of a sensor unit 1e from which breath is introduced to the sensor unit for detection. As shown in FIG. 20B, in order not to be affected by ambient air, or in order for breath to easily reach the sensor unit with an air fan (or a diaphragm pump) even if the transfer tube with a small inner diameter is used, a sample inlet of a sensor unit 1f can be completely covered with a tip end of a sample introduction pipe 32b. However, the sample inlet needs to be covered with a material with an extremely-low water absorption rate or a water absorption rate of 0.

Figure 21:
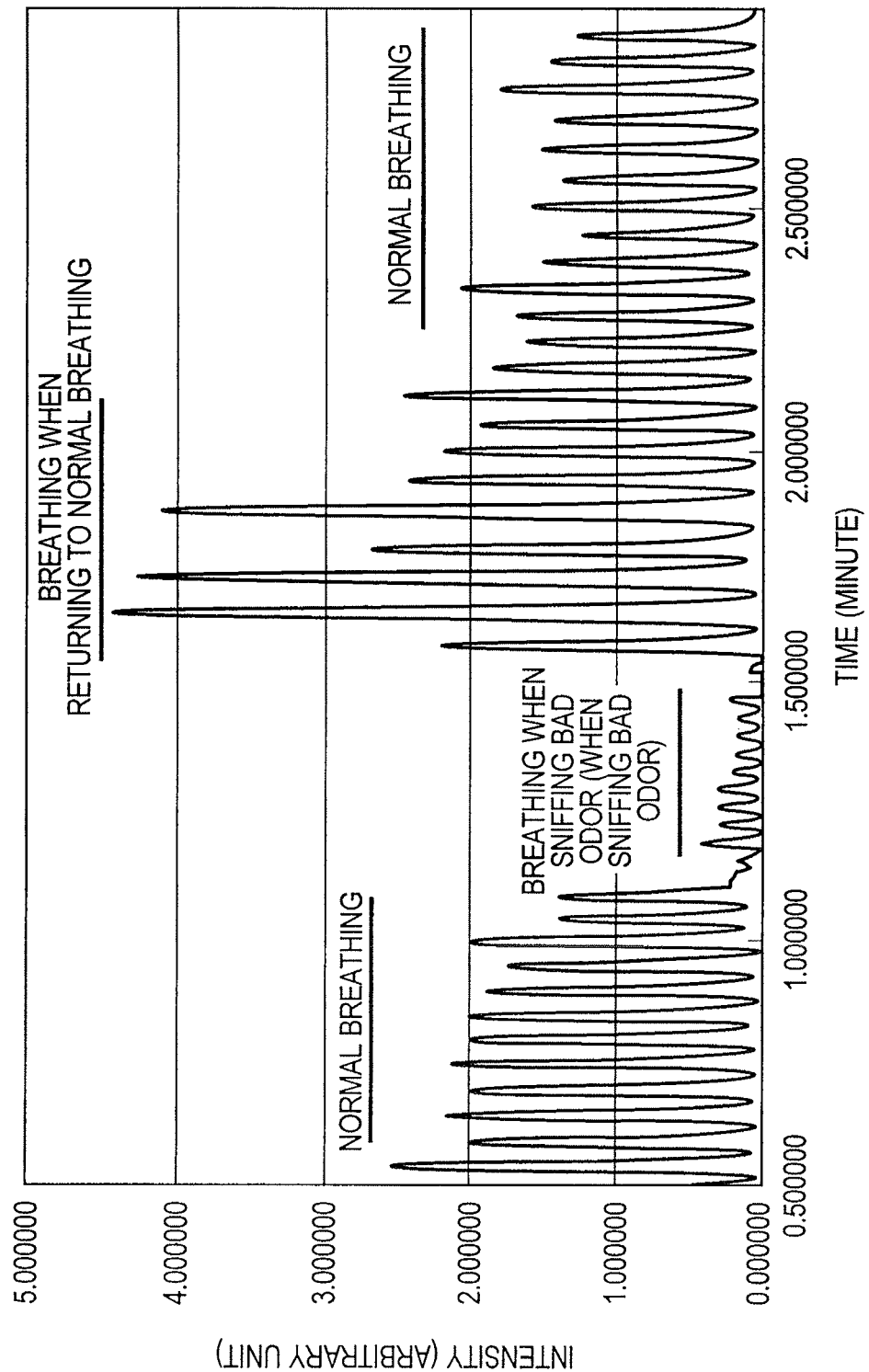
FIG. 21 is a diagram for showing changes in breathing when sniffing a bad odor (ammonia water) in the device of the present invention.
Figure 22:
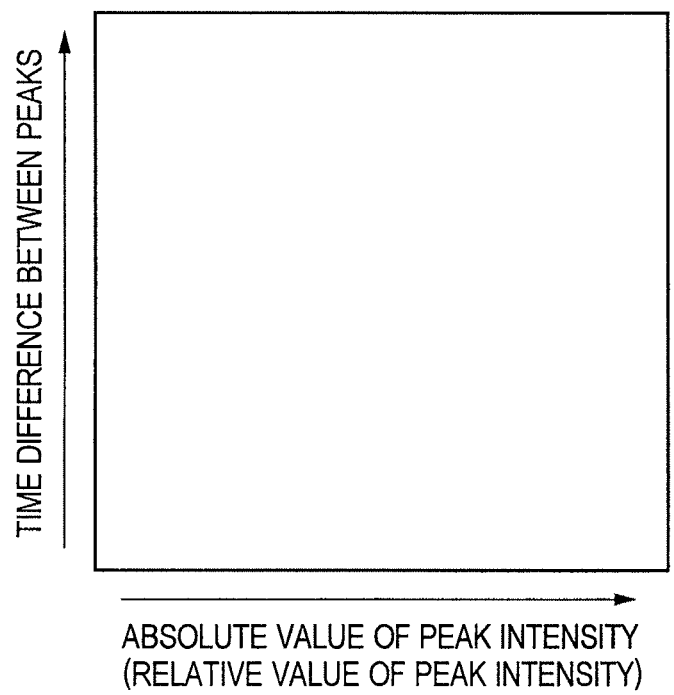
FIG. 22 is a plot diagram between distances between breath peaks and breath peak intensities in the device of the present invention.
Figure 23:
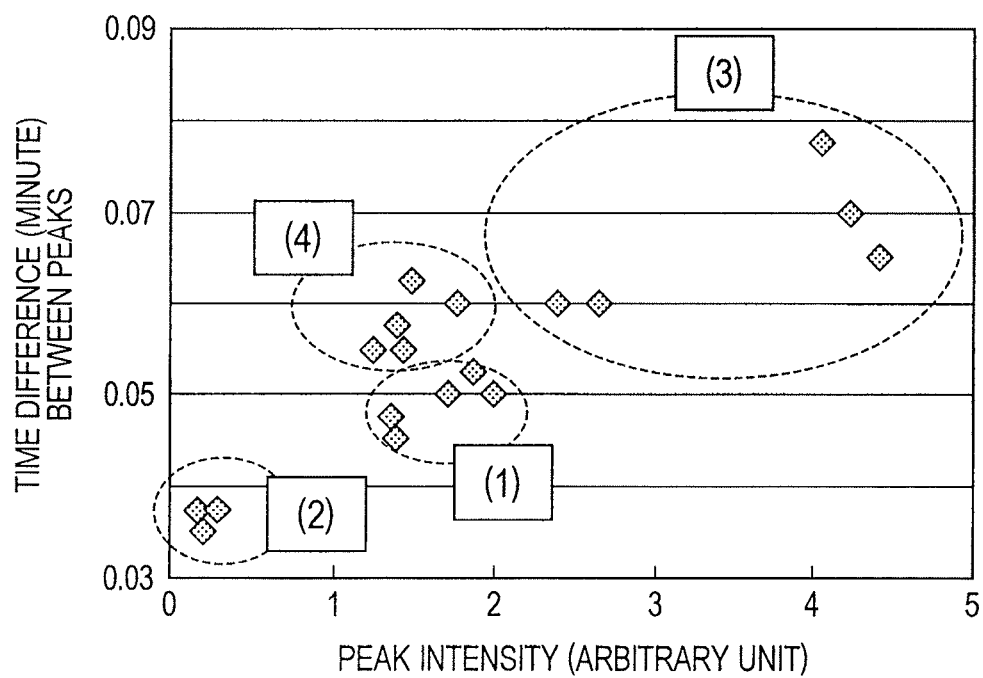
FIG. 23 is a plot diagram of changes in breathing when sniffing a bad odor (ammonia water) in the device of the present invention.

A detection example of breathing measured using the system as shown in FIG. 18 is shown in FIG. 21. If a person suddenly sniffs a bad odor such as ammonia water when breathing normally, the breathing becomes very shallow and rapid so as not to take the bad odor in the body. If the source of the bad odor is removed, the breathing returns to normal breathing through deep and slow breathing. With the use of the present invention, the process can be definitely observed. In order to further understand this, if plotting the graph as shown in FIG. 22 in which the vertical axis represents a time difference between breath peaks and the horizontal axis represents the absolute value or relative value of the peak intensity (time difference-intensity plot), the result as shown in FIG. 23 can be obtained. Specifically, a series of following processes can be definitely understood: normal breathing (area (1)) becomes shallow and rapid breathing (area (2)) if sniffing a bad odor; if the bad odor is removed, the breathing becomes slow and deep (area (3)); and the breathing finally returns to normal breathing (area (4)).

If this is put to practical use, an interest (value judgment of the brain) in videos, music, and the like can be indirectly measured. Generally, a mental activity status in the brain can be considered as an internal expression (image). It is conceivable that such an internal expression (image) of mental emotional information in the brain is externally expressed (external expression of emotional information) through gestures, voice, and the like in addition to language. Breathing is considered as one of them, and an interest (value judgment of the brain) in videos, music, and the like can be indirectly measured by detecting a change in breathing.

Figure 24:
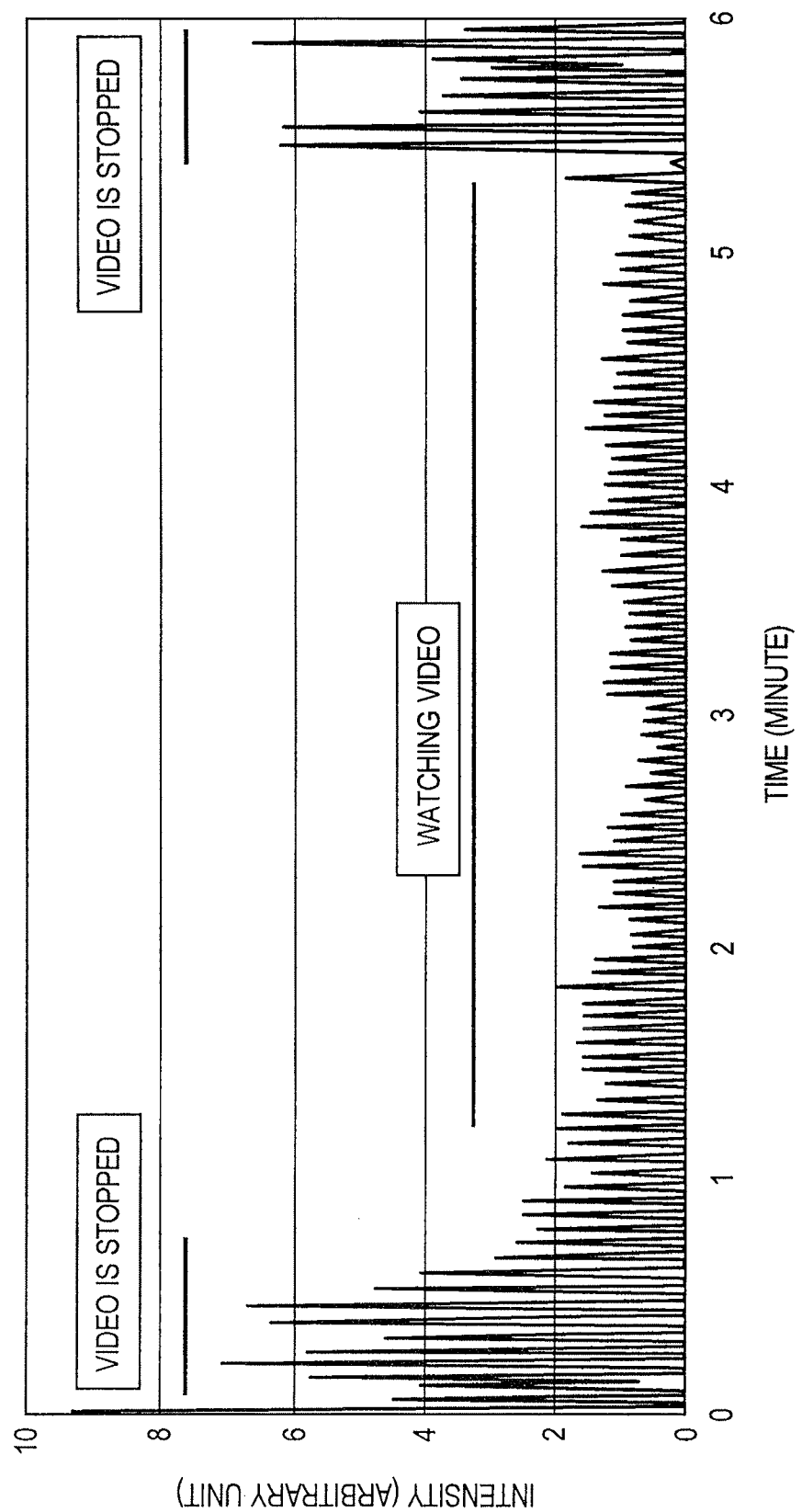
FIG. 24 is a diagram for showing changes in breathing when watching an interesting video in the device of the present invention.
Figure 25:
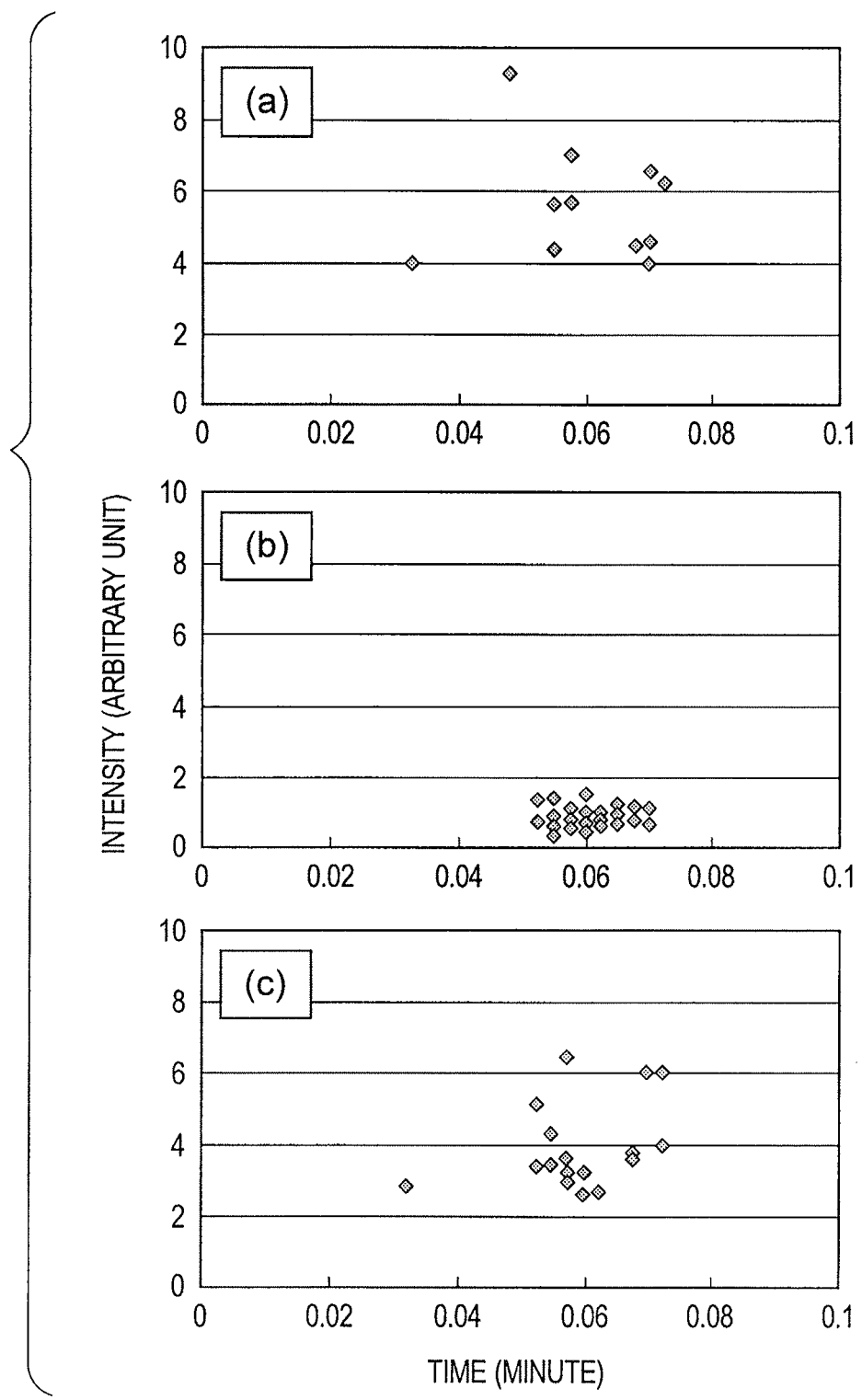
FIG. 25 is a plot diagram of changes in breathing when watching an interesting video in the device of the present invention.

FIG. 24 shows an example thereof. A subject was allowed to watch an interesting video or listen to interesting audio for a certain period of time while breathing normally, and then the video or audio is stopped. If the result is analyzed by the method as shown in FIG. 22, the analysis result as shown in FIG. 25 can be obtained. In FIG. 25, (a), (b), and (c) show the results obtained by performing the time difference-intensity plot for breathing at an initial stage in which a person neither watched an interesting video nor listened to interesting audio, for breathing at a stage in which a person was watching an interesting video or listening to interesting audio, and for breathing at a stage in which a person finished to watch an interesting video or listen to interesting audio. It can be found that the breathing at a stage in which a person was watching an interesting video or listening to interesting audio is apparently changed and the breathing becomes shallow. This probably means that the brain was interested in a video or audio and became tense, leading to a change in breathing.

If such a technique is put to practical use, new marketing using biological reaction can be realized for questionnaire-based marketing.

INDUSTRIAL APPLICABILITY

The present invention can be used for noncontact and non-invasive breath detection. The present invention can be also used for a device for anti-drunk-driving in a mobile object such as an automobile. Further, the value judgment of the brain can be indirectly measured.

What is claimed is:

1. An ion detecting device comprising:
a casing having its inside under atmospheric pressure;
an inlet through which ambient air is introduced into the casing that is placed under atmospheric pressure;
a detection electrode, a voltage applying electrode that is placed opposite to the detection electrode in the casing, an electrode holding unit holding the detection electrode and the voltage applying electrode, and a wall made of the electrode holding unit and placed so as to close the direction which the ambient air is introduced in the casing, wherein the ambient air is ionized in an area between the detection electrode and the voltage applying electrode;
a control unit that generates potential difference between the voltage applying electrode and the detection electrode, and by an electric field created between the voltage applying electrode and the detection electrode, separates the ambient air introduced through the inlet into ions in the casing; and
a current detecting unit connected to the detection electrode and that detects current based on the ions collected by the detection electrode;
wherein the electrode holding unit is made of material with a water absorption rate of 0.4 or smaller.

2. The ion detecting device according to claim 1, wherein a discharging device is provided to prevent the ambient air from remaining in the casing.

3. The ion detecting device according to claim 1, wherein the electrode holding unit is made of ceramic or polyacetal.

4. An ion detecting device comprising:
an inlet through which gas is introduced into a casing that is placed under atmospheric pressure;
a first electrode that traps ions and a second electrode that can apply voltage, the first electrode and the second electrode being placed opposite to each other in the casing and forming an inflow channel for the introduced gas in the direction of the force of gravitation in the casing, wherein the introduced gas is ionized in an area between the first electrode and the second electrode;
a current measurement device that is connected to the first electrode;
a data analyzing device that analyzes components contained in the gas on the basis of a measurement result by the current measurement device, and
an electrode holding unit holding the first electrode and the second electrode, and a wall made of the electrode holding unit and placed so as to close the direction which the gas is introduced in the casing,
wherein the electrode holding unit is made of material with a water absorption rate of 0.4 or smaller.

5. The ion detecting device according to claim 4, wherein the electrode holding unit is made of ceramic or polyacetal.

6. The ion detecting device according to claim 5, further comprising a sensor that detects the ambient air, wherein the sensor is an alcohol sensor.

7. The ion detecting device according to claim 6, wherein a computing device is provided to calculate a breath spectrum on the basis of a signal detected by the sensor.

8. The ion detecting device according to claim 7, wherein breath peaks are specified from the breath spectrum, and time changes of the breath peaks are detected.

9. The ion detecting device according to claim 1, wherein a tube can be connected to the inlet.

10. The ion detecting device according to claim 4, wherein a tube can be connected to the inlet.

* * * * *